US00PP24436P2

(12) United States Plant Patent
Davidson et al.

(10) Patent No.: US PP24,436 P2
(45) Date of Patent: May 13, 2014

(54) ROSE PLANT NAMED 'CA 33'

(50) Latin Name: *Rosa hybrida*
Varietal Denomination: 'CA 33'

(75) Inventors: Campbell G. Davidson, West Hawk Lake (CA); Larry J. Dyck, Morden (CA)

(73) Assignee: Her Majesty the Queen in right of Canada, as represented by the Minister of Agriculture and Agri-Food, Lancombe, Alberta (CA)

( * ) Notice: Subject to any disclaimer, the term of this patent is extended or adjusted under 35 U.S.C. 154(b) by 93 days.

(21) Appl. No.: 13/573,188

(22) Filed: Aug. 29, 2012

(51) Int. Cl.
*A01H 5/00* (2006.01)

(52) U.S. Cl.
USPC ..... Plt./104; Plt./101; Plt./102

(58) Field of Classification Search
USPC ..... Plt./101, 102, 104
See application file for complete search history.

*Primary Examiner* — Susan McCormick Ewoldt
(74) *Attorney, Agent, or Firm* — Penny J. Aguirre

(57) ABSTRACT

A new cultivar of shrub rose, 'CA 33', characterized by its semi-double flowers that are golden yellow in color with a salmon orange blush, its semi-upright plant form, its repeat blooming habit, its satiny foliage with good tolerance to rust and black spot, and its cold hardiness at least to U.S.D.A. Zone 3a.

2 Drawing Sheets

Botanical classification: *Rosa hybrida.*
Variety denomination: 'CA 33'.

BACKGROUND OF THE INVENTION

The present invention relates to a new and distinct cultivar of *Rosa hybrida*. The new cultivar will be referred to hereafter by its cultivar name, 'CA 33'. 'CA 33' is a new cultivar of shrub rose grown for use as a landscape shrub.

The new cultivar of shrub rose is a selection from a controlled breeding program conducted by the Inventors in Morden, Manitoba, Canada with an objective to create a new cultivar of yellow flowering rose that is long blooming with greater hardiness and greater disease resistance.

The new variety of shrub rose, 'CA 33', was selected by the Inventors from amongst seedlings derived from a cross made in March 1996 between the female parent, 'Morden Sunrise' (U.S. Plant Pat. No. 13,969) and the male parent, 'Ausgold' (U.S. Plant Pat. No. 8,688). 'CA 33' was selected as a single unique plant in September 1997.

The new cultivar was first asexually propagated by one of the Inventors by softwood cuttings in Morden, Manitoba, Canada in September 1997. Asexual propagation determined that the characteristics of this cultivar are stable and are reproduced true to type in successive generations.

SUMMARY OF THE INVENTION

The following traits have been repeatedly observed and represent the characteristics of the new shrub rose as observed in Morden, Manitoba, Canada. These attributes in combination distinguish 'CA 33' as a unique cultivar of shrub rose.

1. 'CA 33' exhibits semi-double flowers that are golden yellow in color with a salmon orange blush.
2. 'CA 33' exhibits a semi-upright plant form.
3. 'CA 33' is floriferous with a repeat bloom from the middle of June to the end of September in Morden, Manitoba, Canada.
4. 'CA 33' exhibits satiny foliage.

5. 'CA 33' exhibits cold hardiness at least to U.S.D.A. Zone 3a.
6. 'CA 33' has shown good tolerance to rust and black spot.

The new cultivar of shrub rose can be readily distinguished from its parents. The female parent, 'Morden Sunrise', differs from 'CA 33' in having lighter yellow flowers with pink undertones, less cold hardiness and vigor, and in being less disease resistant. The male parent, 'Ausgold', differs from 'CA 33' in having lighter golden yellow flowers that are larger and more double, a less consistent blooming habit, and much less cold hardiness. 'CA 33' can also be most closely compared to the cultivars 'J. P. Connell' (not patented) and 'RADsun' (U.S. Plant Pat. No. 13,063). 'J. P. Connell' is similar to 'CA 33' in having yellow flowers, but differs from 'CA 33' in having flowers that lighter yellow and lacking an orange tinge, a less compact plant habit, and less disease resistance. 'RADsun' is similar to 'CA 33' in having yellow flowers, but differs from 'CA 33' in having yellow flowers that fade to a cream color, a less consistent blooming habit, a less compact plant habit, and less cold hardiness.

BRIEF DESCRIPTION OF THE DRAWING

The accompanying colored photographs illustrate the overall appearance and distinct characteristics of the new shrub rose, 'CA 33'. The photographs were taken of three year-old plants of 'CA 33' and 'Morden Sunrise' as grown outdoors near Portage la Prairie, Manitoba, Canada.

The photograph in FIG. 1 provides a view of a newly open flower of 'CA 33'.

Figure 1:
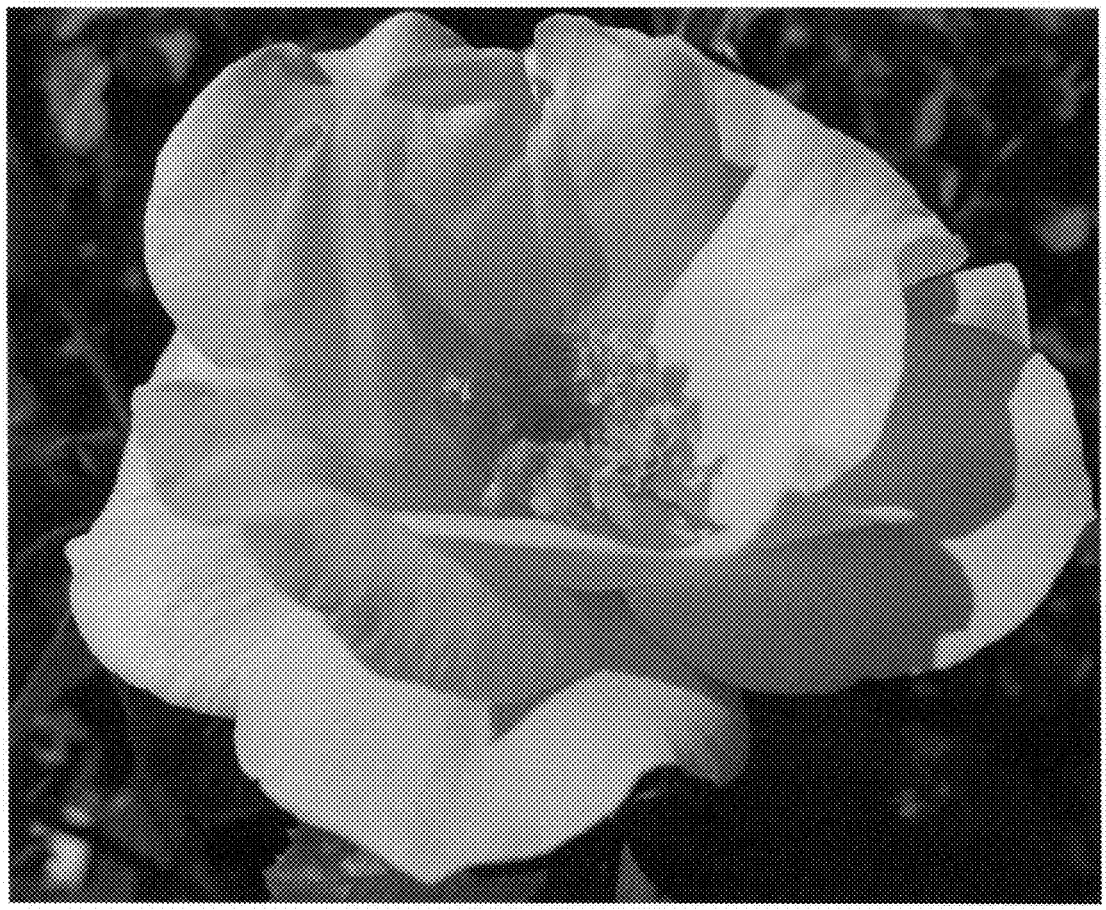
Figure 2:
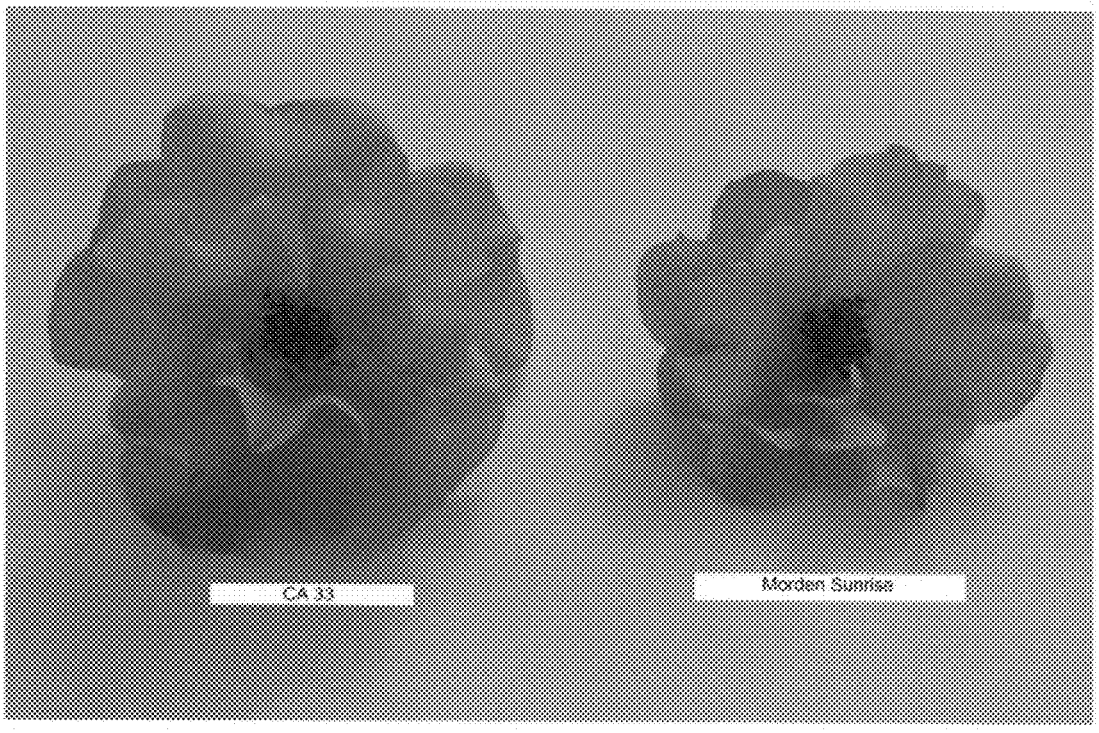

The photograph in FIG. 2 provides a view of a mature flower of 'CA 33' (left) in comparison to a mature flower of 'Morden Sunrise'.

The colors in the photographs are as close as possible with digital photography techniques available, the color values cited in the detailed botanical description accurately describe the colors of the new shrub rose.

DETAILED BOTANICAL DESCRIPTION

The following is a detailed description of two year-old plants the new cultivar as grown outdoors in 2-gallon containers in St Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Repeat bloom from the middle of June to the end of September in Morden, Manitoba, Canada.

*Plant type.*—Deciduous shrub.

*Plant habit.*—Semi-upright.

*Height and spread.*—An average of 40 cm height and width in a 2-gallon container, matures in the landscape up to 90 cm in height and 70 cm in spread.

*Cold hardiness.*—At least to U.S.D.A. Zone 3a.

*Diseases and pests.*—Has shown good tolerance to rust and black spot.

*Propagation.*—Softwood stem cuttings.

*Growth rate.*—Moderate.

Branch description:

*Stem color.*—Young; 144A with small striations of 144D, maturing; 144A with small striations of 144D and very slightly diffused with 183C, mature wood; ridges of 200A and 199D over areas of 144A.

*Stem surface.*—Young and mature; glabrous and slightly satiny, adult wood; finely barked.

*Branching.*—6 lateral stems from base as grow in a 2-gallon container, 0 to 2 secondary stems per lateral stem.

*Stem size.*—An average of 5 mm in width, up to 30 cm in length, secondary stems an average of 15 cm in length and 3 mm in width.

*Thorns.*—None observed.

Foliage description:

*Leaves.*—Division is odd-pinnate, arrangement is alternate, average of 11 cm in length and 6.5 cm in width, internode length is an average of 3.8 cm.

*Leaflets.*—3 to 7, average of 4.5 cm in length and 3 cm in width, broadly elliptic in shape with terminal leaflet broadly elliptic to ovate, rounded base, acute to cuspidate apex, serrated margins with a slight margin of 183B, color emerging leaves upper surface; a blend of 144A and 137B, color emerging leaves lower surface; 146B, color young and mature leaves upper surface; 137A, color young and mature leaves lower surface; 138B, pinnately veined (not conspicuous), mid rib 161B on upper surface and 146C on lower surface, surface glabrous and satiny on upper surface and glabrous and dull on lower surface.

*Rachis.*—Average of 8 cm in length and 1 mm in diameter, color 146C on upper surface and lower surface with center of upper surface suffused with 183B, surface has a few tufts of long hairs on upper and lower surface and small thorns; 1 mm in length and width and 183B in color.

*Stipules.*—Aspect outward with auricle facing outward, adnate to petiole, average of 2.3 cm in length and 5 mm in width, color upper and lower surface; 137B with fine glands on margin 183, surface is glabrous on upper surface and lower surface.

*Petioles and petiolules.*—Petioles; an average of 2.5 cm in length and 1.5 mm in diameter, petiolules; an average of 2 mm in length and 1 mm in diameter, petioles and petiolules; color on mature leaves upper surface; 146C and suffused with 183B, color on mature leaves lower surface; 146C, surface glabrous on upper and lower surfaces.

Inflorescence description:

*Inflorescence type.*—Single, 2, or 3 flowered cyme, semi-double rosette formed flowers.

*Flower number.*—Average of 7 per main stem.

*Flower fragrance.*—Faint rose scent.

*Flower longevity.*—About 8 days, depending on temperature and sunlight exposure.

*Flower type.*—Semi-double.

*Flower size.*—Average of 8.5 cm in diameter and 5.5 cm in depth.

*Peduncles.*—Round in shape, average of 4.5 cm in length and 2.5 mm in diameter, glabrous and satiny surface, 144B in color.

*Bracts.*—2, at base of peduncle, elliptic in shape with long apiculate apex, cuneate-truncate base, margin glandular with glands 183B in color, an average of 2 cm in length and 4 mm in width, a blend of 144A and 137B in color on upper and lower surface, glabrous on both surfaces with a few short fine hairs on margin near apex.

*Flower buds.*—Ovate in shape, an average of 2.8 cm in length and 2.2 cm in width prior to opening, color a blend of 4D, 45C, and 4A, sepal portion a blend of 144A and 137B.

*Sepals.*—5, triangular in shape, margin and tomentose entire, color of upper surface; 138A with margins 155C, color of lower surface; a blend of 144A and 137B, average of 3.6 cm in length and 1.1 cm in width, acuminate apex, truncate base, reflexed to stem on mature flowers, highly pubescent on upper surface, glabrous and satiny on lower surface.

*Petals.*—An average of 10 per flower (including petaloids), drop readily and cleanly, orbicular to obovate in shape with center petaloids irregular but mostly renal in shape, upper surface and lower surface is glabrous, margin entire with occasional slight undulations and notches, base broadly cuneate, apex is rounded, petals an average of 3 cm in length and 2.9 cm in width, petaloids up to 3 cm in length and 1.5 cm in width, color: opening flowers upper surface; 12A and slightly suffused with 26D, 12A at base, opening flowers lower surface; 12D with a slight hint of 26D, 12B at base, fully open flowers upper surface; 4A and suffused with 26D, 12A at very base, fully open flowers lower surface; 8C and very lightly suffused with 26D, 12A at very base, drop without fading.

*Receptacle.*—Average of 1 cm in diameter and 1.5 mm in depth when flower is fully open, donut shaped, waxy surface, 13B in color.

*Pistils.*—About 35 per flower, stigma is an average of 0.5 mm in length and width and 11A in color, style is an average of 8 mm in length, 11D in color and highly pubescent, ovary is cup-shaped, 7 mm in length and 1.3 cm in width, satiny surface and 144A in color.

*Stamens.*—About 65, filaments are about 7 mm in length and 17A in color, anthers are an average of 2.5 mm in length, an average of 2 mm in width and 14C in color, pollen is abundant in quantity and 20B in color.

*Hips.*—Pitcher-shaped, not distinguishing.

It is claimed:

1. A new and distinct cultivar of rose plant named 'CA 33' as herein illustrated and described.

* * * * *